US00PP20713P2

(12) United States Plant Patent
Hanes

(10) Patent No.: US PP20,713 P2
(45) Date of Patent: Feb. 2, 2010

(54) ***VERBENA* PLANT NAMED 'RAP MAGNA'**

(50) Latin Name: *Verbena hybrida×V. tenuisecta*
Varietal Denomination: Rap Magna

(75) Inventor: Mitchell Hanes, Morgan Hill, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/313,826

(22) Filed: Nov. 25, 2008

(51) Int. Cl.
*A01H 5/00* (2006.01)

(52) U.S. Cl. ..... Plt./308

(58) Field of Classification Search ..... Plt./308
See application file for complete search history.

*Primary Examiner*—Annette H Para
(74) *Attorney, Agent, or Firm*—S. Matthew Edwards

(57) ABSTRACT

A new *Verbena* plant named 'Rap Magna' particularly distinguished by red-purple colored flowers, low, compact and outwardly spreading growth habit, medium-green foliage with moderately dissected leaves, free-branching, and tolerance to powdery mildew.

1 Drawing Sheet

Latin name of the genus and species of the plant claimed: *Verbena hybrida×V. tenuisecta.*

Varietal denomination: 'Rap Magna'.

BACKGROUND OF THE NEW PLANT

The present invention comprises a new *Verbena,* botanically known as *Verbena hybrida×V. tenuisecta,* and hereinafter referred to by the variety name 'Rap Magna.'

'Rap Magna' is a product of a planned breeding program. The new cultivar 'Rap Magna' has red-purple colored flowers, low, compact and outwardly spreading growth habit, medium-green foliage with moderately dissected leaves, free-branching, and tolerance to powdery mildew.

'Rap Magna' originated from a hybridization in a controlled breeding program in Gilroy, Calif. USA. Both parent lines contained *V. hybrida* and *V. tenuisecta* background. The female parent was an unpatented, proprietary hybrid seedling identified as '04-1791-5' with light strawberry color. '04-1791-5' has fewer flowers, is later to flower, and has a more open and leggy plant habit than 'Rap Magna.'

The male parent of 'Rap Magna' was an unpatented, proprietary hybrid seedling identified as '03-1752-1' with burgundy color. '03-1752-1' has larger leaves that are not so dissected and fewer flowers than 'Rap Magna.'

'Rap Magna' was selected as one flowering plant within the progeny of the stated cross in February 2006 in a controlled environment in Gilroy, Calif. USA. The pollination took place in August 2005 and the seed sown in November 2005, all in Gilroy, Calif. USA.

The first act of asexual reproduction of 'Rap Magna' was accomplished when vegetative cuttings were taken from the initial selection in February 2006 in a controlled environment in Gilroy, Calif. USA.

Horticultural examination of plants grown from cuttings of the plant initiated February 2006 in Gilroy, Calif. USA, and continuing thereafter, has demonstrated that the combination of characteristics as herein disclosed for 'Rap Magna' are firmly fixed and are retained through successive generations of asexual reproduction.

'Rap Magna' has not been observed under all possible environmental conditions. The phenotype may vary significantly with variations in environment such as temperature, light intensity and day length.

A Plant Breeder's Right for this cultivar was applied for in Canada on Dec. 24, 2007. 'Rap Magna' has not been made publicly available more than one year prior to the filing of this application.

DESCRIPTION OF DRAWING

The accompanying photographic drawing shows typical flower and foliage characteristics of 'Rap Magna' with colors being as true as possible with an illustration of this type.

The photographic drawing shows three flowering potted plants in a hanging basket of the new variety and a close-up of the flowers.

The plants were grown and photographed in Gilroy, Calif. USA in July 2008.

DETAILED BOTANICAL DESCRIPTION

The measurements were taken in Gilroy, Calif. USA in March 2008 on plants that were growing in 4 inch plastic pots in a greenhouse trial. These plants were about 3 months old.

Color Chart used: Royal Horticultural Society Colour Chart (R.H.S.) 2001

BRIEF SUMMARY OF INVENTION

The following observations, measurements, and comparisons describe plants grown in Gilroy, Calif. USA. The following traits have been repeatedly observed and are determined to be basic characteristics of the new variety. The combination of these characteristics distinguishes this *Verbena* as a new and distinct variety.

TABLE 1

DIFFERENCES BETWEEN THE NEW VARIETY 'RAP MAGNA' AND A SIMILAR VARIETY

| | 'Rap Magna' | 'Rap Burg Two' (U.S. Plant Pat. No. 15,743) |
|---|---|---|
| Flower color | Closest to RHS 61A | Closest to RHS 71A |
| Growth habit | More compact | Less compact |
| Leaf size | Smaller | Larger |
| Petiole length | Shorter | Longer |

Plant:

*Plant habit.*—Low, compact and outwardly spreading, free-branching, medium-green foliage, moderately dissected leaves.

*Plant height.*—8–9 cm.

*Plant width.*—25–30 cm.

Foliage:

*Arrangement.*—Opposite, simple.

*Immature, leaf color, upper surface.*—Little lighter than RHS 137A.

*Lower surface.*—RHS 137C.

*Mature, leaf color, upper surface.*—Little deeper green than RHS 137A.

*Lower surface.*—RHS 137C.

*Length.*—2.6–3.2 cm.

*Width.*—2.0–2.7 cm.

*Shape.*—Ovate.

*Base shape.*—Attenuate.

*Apex shape.*—Obtuse to acute.

*Margin.*—Pinnatisect, and irregularly incised.

*Texture, upper surface.*—Hirsute.

*Lower surface.*—Hirsute only along the veins and margins.

*Color of veins, upper surface.*—RHS 144A.

*Color of veins, lower surface.*—RHS 144A.

*Petioles color.*—RHS 144A.

*Petioles length.*—0.7–1.0 cm.

*Diameter of petiole.*—0.15 cm.

*Texture.*—Hirsute.

Stem:

*Quantity of main branches per plant.*—8–10.

*Quantity of leaves per lateral branch.*—8–12.

*Color of stem.*—Little darker than RHS 144A; irregular striations of RHS 166A only on the upper side.

*Length of stem.*—10–16 cm.

*Diameter.*—0.25–0.3 cm.

*Length of internodes.*—1.5–2.5 cm.

*Texture.*—Hirsute.

Inflorescence:

*Type.*—Terminal Raceme.

*Blooming habit.*—Flowers continuously from spring through fall.

*Lastingness of individual blooms on the plant.*—5–7 days in the greenhouse.

*Fragrance.*—None.

*Number of inflorescences per plant.*—25–37 in various stages.

*Color of peduncle.*—RHS 144B.

*Length of peduncle.*—2.5–4.7 cm.

*Peduncle diameter.*—0.15 cm.

*Texture.*—Hirsute; few glandular hairs about RHS 59C.

*Horizontal diameter of inflorescence.*—4.5–5.6 cm.

*Depth of inflorescence.*—2.5–4.5 cm.

*Number of florets per inflorescence* (*including any buds at the time*).—45–62.

Bud (just before opening):

*Color.*—RHS 71A.

*Length.*—1.3–1.4 cm.

*Width.*—0.3 cm.

*Shape.*—Tubular.

Corolla:

*Form.*—Sessile; salverform, composed of 5 petals.

*Immature color, upper surface.*—Closest to RHS 61A but slightly deeper.

*Lower surface.*—RHS 64B; RHS 155B basally.

*Mature color, upper surface.*—Little lighter than RHS 61A; slightly darker at the throat.

*Lower surface.*—Slightly lighter than 64B; RHS 155B basally.

*Floret diameter.*—1.7–1.8 cm.

*Length of petals.*—1.8–1.9 cm.

*Width of petals.*—1.7–1.8 cm.

*Petal shape.*—Obovate.

*Apex shape.*—Emarginate.

*Margin.*—Entire.

*Petal texture, upper surface.*—Papilloase.

*Lower surface.*—Few pilose at attachment to corolla tube.

*Corolla tube length.*—2.0–2.1 cm.

*Corolla tube color inside.*—RHS N155B; hairs at throat are RHS 61A.

*Tube color outside.*—RHS 155B basally and underside; RHS 60C on upper side.

*Corolla texture, inside.*—Hirsute.

*Outside.*—Glabrous; few pilose hairs at corolla flare.

Calyx:

*Type.*—Five sepals whose margins are fused to each other along their length, with a transparent membrane of less than 0.1 cm in width and with one smaller sepal attached to the base of the calyx.

*Color of sepals.*—RHS 138A; RHS 60B anthocyanins at the apex.

*Length of sepals.*—1.0–1.1 cm.

*Width of sepals.*—0.2 cm.

*Sepal shape.*—Linear.

*Apex shape.*—Acute.

*Margins.*—Entire.

*Texture.*—Hirsute; glandular hairs basally of RHS 71A.

Reproductive organs:

*Pistil.*—1.

*Length.*—About 1.3.

*Style color.*—RHS 155C.

*Style length.*—0.9–1.1 cm.

*Stigma color.*—RHS 160A.

*Stamens.*—Anthers and filaments fused to upper half of corolla tube; four anthers with two pollen sacs per anther.

*Color of filaments.*—RHS 155C.

*Length filaments.*—0.1–0.2 cm.

*Length of anthers.*—0.1 cm.

*Anther color.*—RHS 145B.

*Color of pollen.*—RHS 10C.

*Pollen amount.*—Moderate.

*Fertility/seed set.*—Not observed on this hybrid.

Disease/pest resistance: Disease resistance or susceptibility has not been observed on this hybrid.

What is claimed is:

1. A new and distinct variety of *Verbena* plant named 'Rap Magna,' substantially as illustrated and described herein.

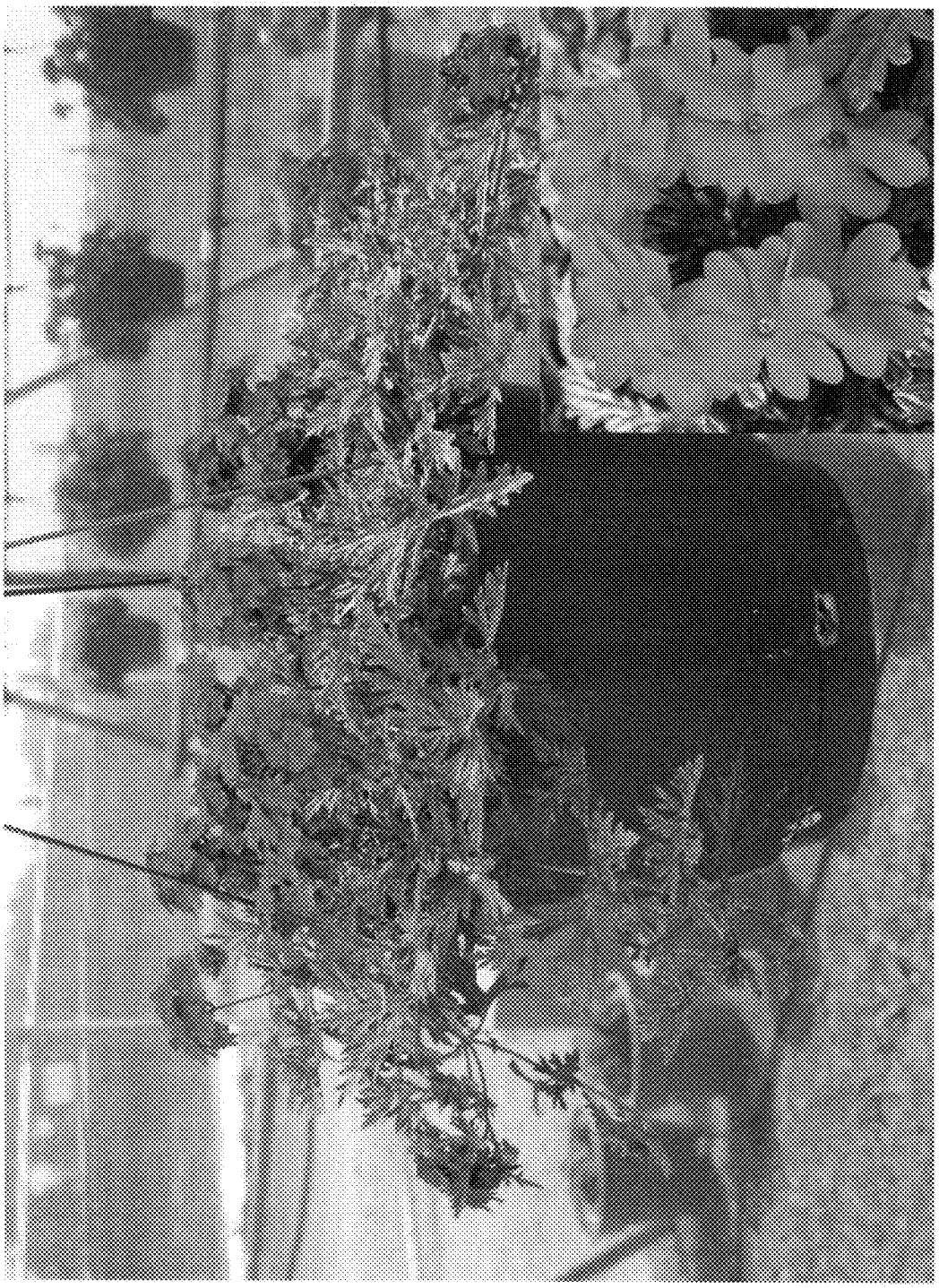

* * * * *